(12) United States Patent
Grimm

(10) Patent No.: US 6,267,726 B1
(45) Date of Patent: Jul. 31, 2001

(54) COVER FOR ULTRASOUND PROBE

(76) Inventor: Peter D. Grimm, 1211 E. Newton, Seattle, WA (US) 98102

( * ) Notice: Subject to any disclaimer, the term of this patent is extended or adjusted under 35 U.S.C. 154(b) by 0 days.

(21) Appl. No.: 09/419,401

(22) Filed: Oct. 14, 1999

(51) Int. Cl.⁷ .................................................. A61B 8/12
(52) U.S. Cl. ............................................ 600/459; 600/462
(58) Field of Search .................... 600/437, 459, 600/462, 587, 372, 478, 439; 428/35.2; 604/22

(56) References Cited

U.S. PATENT DOCUMENTS

| | | |
|---|---|---|
| 4,281,648 | 8/1981 | Rogers . |
| 4,817,616 * | 4/1989 | Goldstein ............................ 600/462 |
| 4,899,737 | 2/1990 | Lazarian . |
| 4,984,582 | 1/1991 | Romanisyzn et al. . |
| 5,509,891 | 4/1996 | DeRidder . |
| 5,842,970 | 12/1998 | Lakusiewicz . |
| 5,997,481 * | 12/1999 | Adams et al. ....................... 600/459 |
| 6,126,607 * | 10/2000 | Whitmore, III et al. ............ 600/459 |

* cited by examiner

Primary Examiner—Marvin M. Lateef
Assistant Examiner—Ali M. Imam
(74) Attorney, Agent, or Firm—Jensen & Puntigam, P.S.

(57) ABSTRACT

The ultrasound probe cover includes a conventional condom which is adapted to fit over an ultrasound probe. The cover is secured to the probe in a water-tight arrangement at the proximal end of the cover by an elastic band. An elongated hollow tube is secured to the inner surface of the cover, which tends to result in an equalization of fluid pressure at both ends of the condom cover during insertion and retraction of the condom into and out of a bodily opening, such as the rectum, of a patient.

6 Claims, 1 Drawing Sheet

COVER FOR ULTRASOUND PROBE

TECHNICAL FIELD

This invention relates generally to probes for ultrasound devices, and more specifically concerns an ultrasound probe cover.

BACKGROUND OF THE INVENTION

Ultrasound devices are widely known and used in a variety of applications, including a number of specific applications in the medical field. In some medical applications, the ultrasound probe is positioned on the skin surface of the human body, while in other cases, the probes are designed to be inserted into openings in the human body, such as for instance the rectum, in the diagnosis and treatment of prostate cancer. In such applications, there is a need for an inexpensive, single-use cover for the ultrasound probe, as discussed in more detail below.

The cover must be easy to put on the probe and remove therefrom and be very inexpensive. Further, it must be waterproof and tough enough to reliably withstand the single use without tearing or breaking. In many cases, a very thin elastic rubber member, such as a conventional condom, is used. The condom cover protects both the probe and the patient as well as providing a capability for having water or other fluid around the tip of the probe. Having fluid around the tip of the probe is important, as it improves the transmission of the sound waves to and from the tissue of interest, and thus improves the image quality.

A significant disadvantage of such a cover arrangement, however, is that fluid initially present at the distal end of the condom cover, at the tip of the probe, is forced away from the tip of the probe, toward the proximal end of the probe cover, during insertion of the probe into the rectum of the patient.

Some manufacturers have attempted to solve this problem by having a channel in the probe itself, extending from the proximal end to the tip. Water is then injected through the probe into the space between the cover and the probe tip. While this arrangement improved the contact of the probe with the rectum, it often resulted in distortion of the prostate, particularly at the apex portion thereof. This distortion is quite disadvantageous relative to treatment of prostate cancer using radioactive seed therapy, which requires an accurate and undistorted image of the prostate.

Most of the modern ultrasound probes do not have such a fluid channel. Therefore, if fluid is to be used to improve signal transmission in current probes, the technician must put the fluid into the condom prior to securing it to the probe. As indicated above, however, in the process of inserting the probe with the cover into the rectum, most if not all of the water initially present at the tip of the probe is forced rearwardly to the proximal end of the cover. This eliminates the possibility of improved transmission resulting from fluid at the tip of the probe, because of the movement of the fluid to the proximal end of the cover.

The "bunching" of the fluid at the proximal end of the probe can also result in the insertion of the probe being more difficult and can further result in tearing of the cover, as well as other disadvantages.

Hence, it is desirable to have an ultrasound cover which has the physical characteristics of a conventional condom, but which is adapted so that fluid can remain near the distal end of the probe, without distorting the prostate, during insertion and retraction of the probe.

DISCLOSURE OF THE INVENTION

Accordingly, the invention is a cover for an ultrasound probe, comprising: a thin, flexible cover member adapted to fit over an ultrasound probe member, wherein the cover member is secured to the ultrasound probe in use by a securing element in the vicinity of a proximal end of the cover member; and an elongated hollow member secured to an inner surface of the cover member and extending lengthwise therealong, wherein when the ultrasound probe with the cover member and with fluid present between the probe and the cover member is moved into and out of a bodily opening, fluid moves through the hollow member, tending to equalize fluid pressure at both ends of the cover member during insertion and retraction of the probe and cover member into and out of the bodily opening.

BEST MODE FOR CARRYING OUT THE INVENTION

Figure 1:
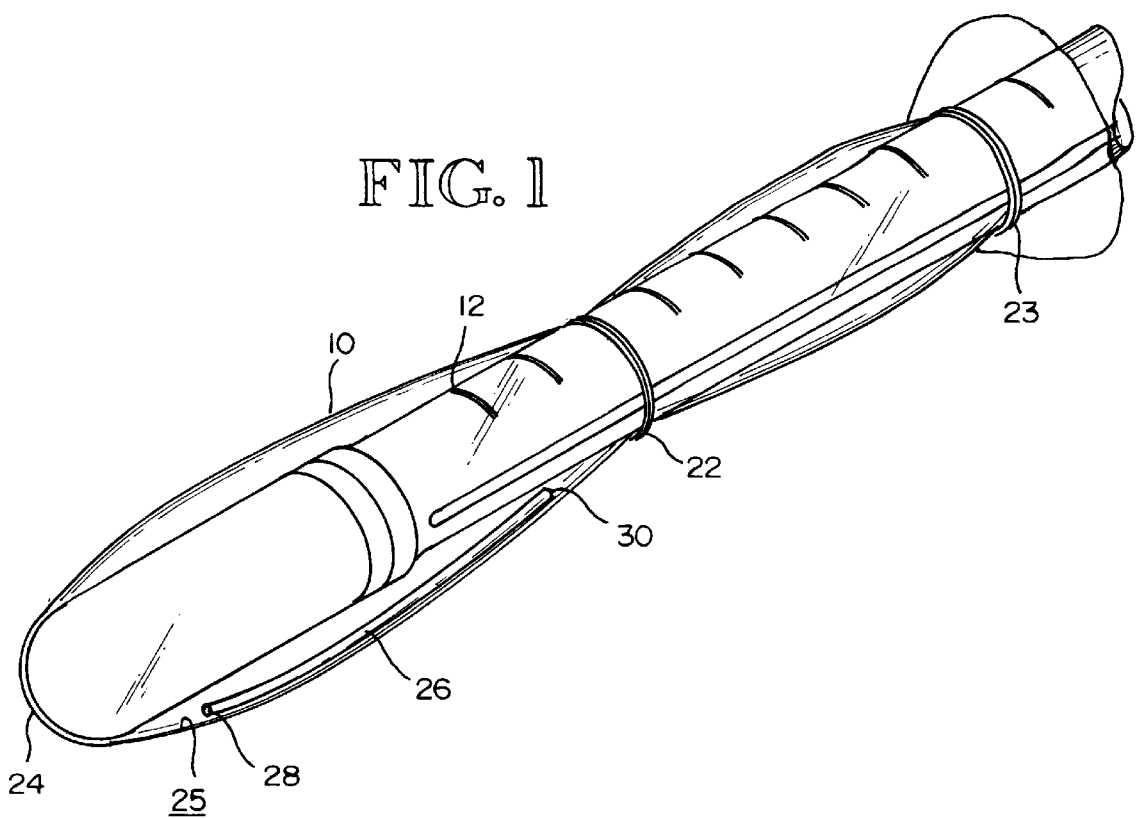
FIG. 1 is an isometric view of the ultrasound cover of the present invention shown in place on a conventional ultrasound probe.
Figure 2:
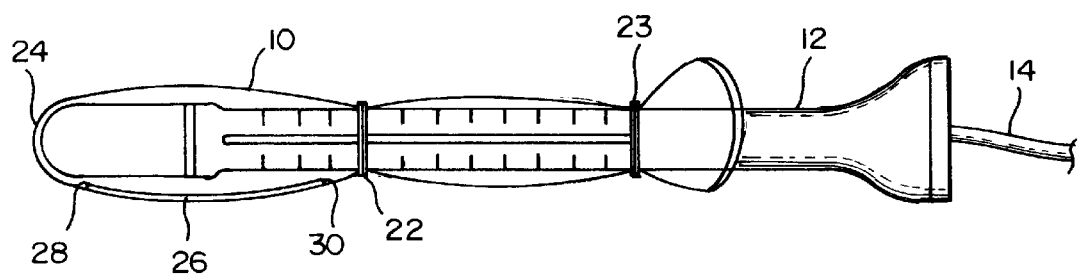
FIG. 2 is a side elevational view of the ultrasound probe cover of FIG. 1.

FIGS. 1 and 2 show the ultrasound probe cover of the present invention. The probe cover, shown generally at 10, is used with a conventional ultrasound probe 12, which in the embodiment shown is generally cylindrical, approximately 7 inches long and 1¼ inches in diameter. The ultrasound probe 12 is a conventional ultrasonic transducer, which in operation transmits and receives ultrasound signals to and from the human body. The ultrasound probe 12 is connected via a cable 14 to a conventional ultrasound device which generates the ultrasound signals to be transmitted and then processes the returned signals for display as an image for the user. All of the above is conventional and well-known.

The ultrasound device in one particular application for which the probe cover is useful involves the diagnosis and treatment of prostate cancer. Using a technique known as brachytherapy, the ultrasound probe is inserted into the rectum of a patient and ultrasound signals are used to image the prostate gland. Accurate ultrasound imaging permits the physician to accurately position needles and the radioactive seeds placed therein within the prostate in accordance with a prescribed plan. This application is just one specific illustration of the uses of ultrasound, and is explained in more detail in U.S. Pat. No. 5,938,583, assigned to the same assignee as the present invention.

It should be understood, however, that the brachytherapy application described above is only one example, as ultrasound has a variety of applications. The probe cover of the present invention may be useful in several different ultrasound applications.

The probe cover 10 of the present invention includes a conventional condom. The condom is used, as noted above, because it has a number of characteristics which are important for a successful probe cover. First, the condom is flexible, pliable, and yet is reasonably tough and difficult to break. The condom cover is very thin so that it does not interfere with the normal insertion and retraction (removal) of the probe. The condom is also waterproof and has a certain amount of stretchability Typically, the condom is made from latex material.

It should, however, be recognized that while existing condoms are suitable for use in the present invention, other cover members having similar characteristics can certainly be used. In the embodiment shown, the condom is approximately 7 inches long and approximately 1¼ inches in diameter. Being a condom, it meets all the physical requirements of the ultrasound probe cover discussed above, including, specifically, flexibility. Probe cover 10 is attached to the probe 12 toward the proximal end of the cover, in a waterproof arrangement. The probe cover is filled with approximately 20 cc of fluid (although this amount could vary to some extent), such as water. An elastic band 22, with a diameter slightly less than the diameter of the probe, is typically used, so that cover 10 is held tightly against the exterior surface of the ultrasound probe 12. A second elastic band 23 can be used, if desired, quite near the inboard (proximal) end of cover 10.

With the arrangement shown, condom cover 10 is in essence free-floating from elastic band 22 to the distal end 24 of the cover, i.e. the cover is not secured to the probe from band 22 to the end of the cover. Attached to an inner surface 25 of probe cover 10 is a small diameter, elongated tube 26. Tube 26 is positioned approximately midway between elastic band 22 and distal end 24 of probe cover 10. In the embodiment shown, tube 26 is approximately 3½ inches long, which results in a significant space between the respective ends 28, 30 of tube 26 and the elastic band 22 and distal end 24 of the cover 10, respectively.

In the embodiment shown, tube 26 is a 23-gauge plastic tube, having an outside diameter of 2 millimeters and an internal diameter of 1.1 millimeters. These dimensions, however, can be varied to some extent. Tube 26 is secured to the inner surface of the cover 10 by various means, such as tape and glue, among others.

In use, the probe cover 10 with attached internal tube 26 is placed around the ultrasound probe and elastic band 22, holding the cover 10 on the probe 12 in a waterproof relationship. The probe with probe cover 10 in place are now ready for use in a particular application. As indicated above, in the brachytherapy application, the probe is inserted into the rectum, filled with approximately 20 cc of fluid, such as water, at the distal end, to improve transmission of ultrasound signals to and from the ultrasound probe.

During insertion of the probe into the rectum, fluid at the distal end of the condom is initially forced into the space between the rectal opening and elastic band 22. The tube 26, secured to the cover, extends from a point within the rectum to a point outside the rectal opening. The tube 26 during the process of insertion of the probe remains open. Fluid can move freely between the end of the tube closest to the tip of the probe and the end which is outside the rectal opening, near band 22 and vice versa. The fluid present at the distal end of the cover provides the necessary fluid contact between the ultrasound probe and the rectal mucosa. Equal fluid pressure is maintained at both ends of the cover by tube 26, since fluid is free to move through the tube, regardless of the position of the probe, preventing excessive fluid at the distal end of the cover and subsequent distortion of the prostate itself as the probe is moved.

The presence of the open tube in the arrangement shown also prevents the condom cover from bunching up at insertion or removal at either end thereof and thereby promotes the ease of insertion of the probe. The desired ultrasound procedure may then be carried out in conventional fashion. When the procedure is completed, the probe with the cover is retracted, bands 22 and 23 (if a band 23 is used) loosened and the probe cover discarded.

Although a preferred embodiment of the invention has been disclosed herein for illustration, it should be understood that various changes, modifications and substitutions may be incorporated in such embodiment without departing from the spirit of the invention, which is defined by the claims as follows.

What is claimed is:

1. A cover for an ultrasound probe, comprising:

a thin, flexible cover member adapted to fit over an ultrasound probe member, wherein the cover member is secured to the ultrasound probe in use by a securing element at a selected point along the length of the cover member from a distal end of the cover member; and an elongated, hollow member, open at both ends, positioned entirely within an interior volume of the cover member, between the distal end of the cover member and said selected point along the length of the cover member, the hollow member extending lengthwise along the cover member, wherein when the ultrasound probe with the cover member with fluid present between the probe and the cover member is moved into and out of a bodily opening, fluid moves through the hollow member, tending to equalize fluid pressure between the distal end of the cover member and said selected point along the length of the cover member, during insertion and retraction of the probe and cover member into and out of the bodily opening.

2. An article of claim 1, wherein the hollow member is a small diameter tube.

3. An article of claim 2, wherein the internal diameter of the tube is approximately 1.1 millimeters.

4. An article of claim 1, wherein the cover member is secured to the ultrasound probe in use in a water-tight relationship by the securing element.

5. An article of claim 1, wherein the cover member is a conventional condom.

6. An article of claim 1, wherein the hollow member has a length which is approximately one-half the overall length of the cover member, and is located approximately mid-length of the probe.

* * * * *